United States Patent [19]

Terashima et al.

[11] 4,338,255
[45] Jul. 6, 1982

[54] MODIFIED LITHIUM ALUMINUM HYDRIDES

[75] Inventors: Shiro Terashima; Norihiko Tanno; Kenji Koga, all of Tokyo, Japan

[73] Assignee: Sumitomo Chemical Company, Limited, Osaka, Japan

[21] Appl. No.: 238,136

[22] Filed: Feb. 25, 1981

[30] Foreign Application Priority Data

Mar. 4, 1980 [JP] Japan .................................. 55-27673
Jul. 18, 1980 [JP] Japan .................................. 55-98956

[51] Int. Cl.$^3$ ............................................... C07F 5/06
[52] U.S. Cl. ............................ 260/448 AD; 568/630
[58] Field of Search ..................... 260/448 R, 448 AD

[56] References Cited

U.S. PATENT DOCUMENTS 3,048,612 8/1962 Walde ........................... 260/448 AD
3,787,450 1/1974 Casensky et al. ............ 260/448 AD
3,933,879 1/1976 Langer, Jr. et al. ............ 260/448 R
4,284,581 8/1981 Noyori .......................... 260/448 AD

OTHER PUBLICATIONS

Tetrahedron Letters, No. 24, 2065–2068, (1974).
Tetrahedron, vol. 32, 939–944, (1976).
Tetrahedron Letters, No. 29, 2683–2686, (1979).
Tetrahedron Letters, vol. 21, 1735–1738, (1980).
Chemistry Letters, 783–784, (1979).
Bull. Chem. Soc. Japan, vol. 51, 1869–1873, (1978).
Heterocycles, vol. 12, No. 4, 499–502, (1979).
J. Am. Chem. Soc., vol. 101, 3129–3131, 5843–5844 (1979).

Primary Examiner—Thomas A. Waltz
Assistant Examiner—Raymond Covington
Attorney, Agent, or Firm—Stevens, Davis, Miller & Mosher

[57] ABSTRACT

Novel modified lithium aluminum hydride type reducing agents obtained by reacting one equivalent of lithium aluminum hydride with one equivalent of an optically active N-substituted ephedrine of the formula,

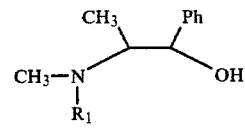

(wherein $R_1$ is a $C_1$–$C_4$ alkyl group or benzyl group, and Ph is phenyl group)

and two equivalents of an N-substituted aniline of the formula,

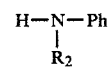

(wherein $R_2$ is $C_1$–$C_4$ alkyl group or phenyl group, and Ph is phenyl group).

This reducing agent is usable for reducing the organic compounds having a carbonyl group (ketone group or aldehyde group) in their structure into the corresponding alcohols. It is particularly useful as a reducing agent for asymmetrically reducing the unsymmetrical ketones to selectively produce either an alcohol in which the asymmetric carbon atom bonded to the hydroxy group is in R-configuration or an alcohol in which said asymmetric carbon atom is in S-configuration.

9 Claims, No Drawings

MODIFIED LITHIUM ALUMINUM HYDRIDES

This invention relates to a novel reducing agent which can be used for reducing the organic compounds having a carbonyl group (ketone group or aldehyde group) in their structure into the corresponding alcohols and which is particularly useful as a reducing agent for asymmetrically reducing the unsymmetrical ketones to selectively give an alcohol in which the asymmetric carbon atom bonded to the hydroxy group is in R-configuration or an alcohol in which said asymmetric carbon atom is in S-configuration. That is, the invention relates to a novel lithium aluminum hydride type reducing agent partially decomposed by using one equivalent of an optically active N-substituted ephedrine and two equivalents of an N-substituted aniline. More particularly, this invention relates to a novel modified lithium aluminum hydride type reducing agent obtained by reacting one equivalent of lithium aluminum hydride with one equivalent of an optically active N-substituted ephedrine of the formula (I),

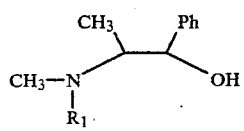

(wherein $R_1$ is a $C_1$-$C_4$ alkyl group or benzyl group, and Ph is phenyl group) and two equivalents of an N-substituted aniline of the formula (II),

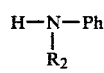

(wherein $R_2$ is a $C_1$-$C_4$ straight chain alkyl group or phenyl group, and Ph is phenyl group).

The optically active N-substituted ephedrine represented by the above-shown formula (I) is either a (−)-isomer or a (+)-isomer. The $C_1$-$C_4$ alkyl group represented by $R_1$ in the above-shown formula (I) may be properly selected from the straight chain or branched chain alkyl groups such as methyl, ethyl, propyl, isopropyl, butyl, tert-butyl, iso-butyl, sec-butyl, etc., but the methyl group is preferred. As for the $C_1$-$C_4$ alkyl group represented by $R_2$ in the above-shown formula (II), there may be recited the straight chain alkyl groups such as methyl, ethyl, propyl, butyl, etc., but a methyl or ethyl group is preferred, the latter being more preferred.

There are known a number of reagents capable of reducing the carbonyl group of an organic compound having a ketone structure ($>C=O$) or an aldehyde structure

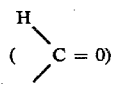

into a hydroxy group. As such reagents, there may be recited, for example, sodium borohydride, potassium borohydride, lithium borohydride, zinc borohydride, sodium cyanoborohydride, lithium aluminum hydride, lithium tri-tertbutoxyaluminum hydride, lithium trimethoxyaluminum hydride, sodium bis(2-methoxyethoxy)aluminum hydride, sodium aluminum hydride, etc. However, when an unsymmetrical ketone reducing reaction is performed by using such reducing agents, the resulting product becomes an equal-weight mixture, namely a racemate, of an alcohol in which the asymmetric carbon atom bonded to the hydroxy group is R-configuration and an alcohol in which said asymmetric carbon atom is in S-configuration. In contrast with this, when an unsymmetrical ketone reducing reaction is conducted by using the reducing agent of this invention, there takes place an asymmetric reduction to allow much stereo-selective formation of either an alcohol in which the asymmetric carbon atom bonded to the hydroxy group is in R-configuration or an alcohol in which said asymmetric carbon atom is in S-configuration.

Many efforts have been made toward development of the reagents for asymmetric reduction of unsymmetrical ketones. Particularly, lots of tests have been pursued on the modified lithium aluminum hydrides formulated by partially decomposing lithium aluminum hydrides with an optically active compound, and some asymmetrical reducing reagents with good selectivity have been worked out. However, any of the hitherto proposed reagents has some defects as mentioned below.

For example, Vigneron et al have worked out a modified lithium aluminum hydride partially decomposed by using N-methyl-ephedrine and 3,5-dimethylphenol (I. Jacquet and J. P. Vigneron: Tetrahedron Letters, 1974, 2065; J. P. Vigneron and I. Jacquet: Tetrahedron, 32, 939 (1976); J. P. Vigneron and V. Bloy: Tetrahedron Letters, 1979, 2683; Idem., Ibid., 1980, 1735), but this preparation involves the following problems. The 3,5-dimethylphenol used as additive is bound to mix in the reduction product alcohol and difficult to separate. Also, its reducing power is weak, and reduction of an $\alpha,\beta$-unsaturated ketone, aldehyde or the like results in a poor chemical yield.

Another modified lithium aluminum hydride partially decomposed with a proline derivative has been worked up by Mukaiyama et al (T. Mukaiyama, M. Asami, J. Hanna and S. Kobayashi: Chemistry Letters, 1979, 783; M. Asami, H. Ohono, S. Kobayashi and T. Mukaiyama: Bull. Chem. Soc. Japan, 51, 1869 (1978); M. Asami and T. Mukaiyama: Heterocycles, 12, 499 (1979)), but this preparation has defects that the proline used as asymmetry source is expensive and that several steps are required for the synthesis thereof.

Also lately, a modified lithium aluminum hydride partially decomposed with a binaphthyl alcohol derivative and an alcohol was proposed by Noyori et al (R. Noyroi, I. Tomino and Y. Tanimoto: J. Am. Chem. Soc. 101, 3129 (1979); R. Noyori, I. Tomino and M. Nishizawa: Ibid., 101, 5843 (1979)), but this proposal has the drawbacks that the asymmetry source must be synthesized and resolved, that difficulties attend the separation of the reduction product alcohol and that its chemical yield is poor.

The present inventors have devoted themselves to the study aimed at overcoming the above-shown problems and working out an excellent modified lithium aluminum hydride type reducing agent which can meet all of the following three requirements:

1. The reduction reaction proceeds with a high chemical yield and a high asymmetry yield.

2. The yielded alcohol product can be easily separated from the asymmetry source and other additives used.

3. The asymmetry source used is available in large quantities and at low cost, and it can be also easily recovered with a high optical purity and in a high yield after completion of the reaction and can be reused.

As a result, the present inventors have found an excellent modified lithium aluminum hydride type reducing agent which is free of the defects of the conventional modified lithium aluminum hydride type reducing agents and which meets all of the above-said three requirements and is commercially practiceable, and completed the present invention.

The reducing agent according to this invention can be obtained by reacting one equivalent of lithium aluminum hydride with one equivalent of an optically active N-substituted ephedrine of the afore-shown general formula (I) and two equivalents of an N-substituted aniline represented by the afore-shown general formula (II).

The reaction is carried out under an anhydrous condition in an atmosphere of an inert gas such as nitrogen or argon gas.

The reaction solvent used in the process of this invention is not subject to any specific restrictions provided that it does not take any part in the reaction, and there may be used, for example, a solvent such as dimethyl ether, diethyl ether, tetrahydrofuran, diglyme, methylal, toluene or the like, but among them, diethyl ether is preferred.

The reaction can be safely conducted at a temperature of from 0° to 100° C., but it is recommended to use a temperature of from room temperature to 40° C.

The reaction time is not specifically limited, and a one- to three-hour reaction will suffice.

The N-methylephedrine represented by the general formula (I) wherein $R_1$ is a methyl group can be easily synthesized by a one-step treatment only comprising reductive methylation of a corresponding readily accessible unexpensive (+)- or (−)-ephedrine with formaline-formic acid (K. Nakajima: Journal of the Chemical Society of Japan, 81, 1476 (1960)).

The lithium aluminum hydride employed for the preparation of such modified lithium aluminum hydride type reducing agents is usually used in the form of a solution, but according to the present invention, it is not necessarily used as a solution; it can as well be used as a suspension in a reaction solvent, which widens the industrial versatility of the process of this invention.

The thus obtained modified lithium aluminum hydride type reducing agents according to this invention are believed to have a chemical structure expressed by the following formula (III),

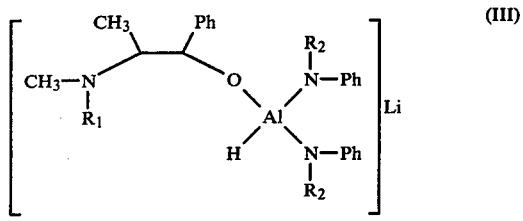

(wherein $R_1$, $R_2$ and Ph are as defined above).

The reducing agent of this invention prepared in the manner described above is usually not isolated from the reaction solution but is immediately used for the ensuing reduction reaction.

The reducing agent of this invention is usable as a reducing agent for converting the carbonyl group in an organic compound having a ketone or aldehyde structure into a hydroxy group. It is specifically noteworthy that the product of this invention can be used as an asymmetric reduction agent for the unsymmetrical ketones, namely, the compounds having a ketone structure which produces the asymmetric center as a result of reduction.

In the course of the reduction of an organic compound, there takes place no side reaction and the carbonyl group alone is reacted even if such compound has in its structure a functional group such as ester, carboxylic acid, amide, olefin or the like, so that the product of this invention can be applied to all sorts of organic compounds having a ketone or aldehyde structure. The preferable organic compounds are the unsymmetrical ketone compounds having a ketone structure which produces the asymmetric center as a result of the reduction.

The reduction employing the reducing agent of this invention is carried out by using said reducing agent and an organic compound having a ketone or aldehyde structure under anhydrous conditions in an atmosphere of an inert gas such as nitrogen or argon gas.

The amount of the reducing agent of this invention used in the reaction may be of any ratio greater than one equivalent to one equivalent of the organic compound, but a ratio of 1–5 equivalents to one equivalent of the organic compound is preferred.

The reaction solvent used in this invention is not subject to any specific restrictions provided that it does not participate in the reaction. There may be used, for example, dimethyl ether, diethyl ether, tetrahydrofuran, diglyme, methylal, toluene, etc., but diethyl ether is preferred.

The reaction temperature is within the range of −100° to 100° C., and a temperature of from −78° to −100° C. is preferred for an asymmetric reduction reaction.

The reaction time, although not limited specifically, may be 1 to 6 hours.

After performing the reduction reaction under the above-said conditions, the reaction solution is added with an aqueous solution of a mineral acid such as hydrochloric acid or sulfuric acid and the organic solvent layer is separated, followed by drying and distilling-off of the organic solvent, whereby the desired alcohol compound alone can be readily obtained in a high yield.

The optically active N-substituted ephedrine (I) and N-substituted aniline (II) used in the reaction can be recovered as a mixture in an almost quantitative yield by merely adding an alkaline aqueous solution such as an aqueous sodium hydroxide solution or an aqueous potassium hydroxide solution to the above-said aqueous layer, extracting the mixed solution with an organic solvent such as ethyl acetate, etc. which can dissolve the optically active N-substituted ephedrine (I) and N-substituted aniline (II), then drying the extract and distilling off the organic solvent. Also, they can be recovered separately by means of distillation under reduced pressure.

In this way, the N-substituted ephedrine (I) can be recovered in an optical purity without accompanying racemization and can be reused as it is.

As an embodiment of use of the reducing agent of this invention, it is used in a reaction for obtaining 2-(1′-hydroxy)ethyl-5,8-dimethoxy-3,4-dihydronaphthalene of the formula (V),

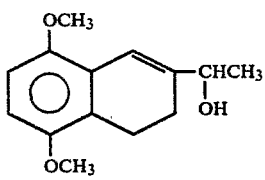

(V)

by reducing the carbonyl (>CO) portion of 2-acetyl-5,8-dimethoxy-3,4-dihydronaphthalene of the formula (IV),

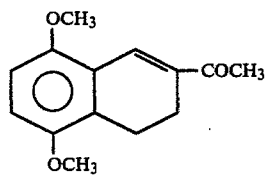

(IV)

In the case of the reducing agent of this invention using a (—)-isomer ((—)-1(R),2(S)-N(C$_1$–C$_4$) alkyl- or benzyl-substituted ephedrine) as the N-substituted ephedrine of the formula (I), such reducing agent may be used for performing an asymmetric reduction of the compound of the formula (IV) to give (—)-2-(1'(S)-hydroxy)-ethyl-5,8-dimethoxy-3,4-dihydronaphthalene of the formula (V'),

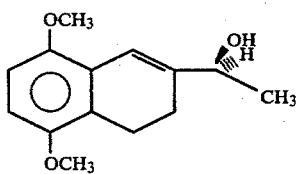

(V')

This asymmetric reduction is performed at −78° C. for 3 hours and the neutral portion is separated from the reaction product to obtain a crude compound of the formula (V'). Also, (—)-N-methylephedrine and N-ethylaniline are recovered quantitatively from the basic portion of the reaction product.

Recrystallization of the crude compound (V') from n-hexane gives the compound (V') of 100% optical purity, m.p.: 88°–89° C., $[\alpha]_D^{20} - 20.5°$ (C=1.07, ethanol).

Examples of (—)-N-(C$_1$–C$_4$) alkyl- or benzyl-substituted ephedrines usable for the preparation of said reducing agent of this invention are (—)-N-methylephedrine, (—)-N-ethylephedrine (O. Červinka, et al: Coll. Czech Chem., Comm., 32, 3897 (1967)), (—)-N-propylephedrine, (—)-N-isobutylephedrine, (+)-N-benzylephedrine (S. Yamada et al: Yakugaku Zasshi, 100, 319 (1980)). Among them, (—)-N-methylephedrine is the most preferred asymmetry source. As examples of N-mono-(C$_1$–C$_4$) alkyl- or benzyl-substituted anilines, one may recite, beside N-ethylaniline, the following: N-methylaniline, N-propylaniline, N-isopropylaniline, N-butylaniline, N-isobutylaniline, N-ethyl-3,5-dimethylaniline, N-ethyl-2,6-dimetylaniline, diphenylamine, carbazole, etc., but the asymmetry yield of the compound (V') was best when N-ethylaniline was used. In case of using n-t-butylaniline, pyrrolidine, piperidine, morpholine, pyrrole, imidazole, benztriazole or the like in place of N-ethylaniline, there took place no desired reduction reaction or, even though the reaction advanced, the asymmetry yield was low.

The compound of the formula (V) (particularly (V')) is an intermediate product in the course of the preparation of 2-acetyl-5,8-dimethoxy-1,2,3,4-tetrahydro-2-naphthol of the formula (1),

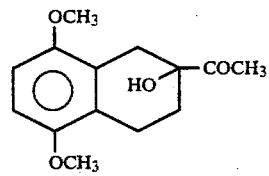

(1)

particularly, (—)-2(R)-acetyl-5,8-dimethoxy-1,2,3,4-tetrahydro-2(R)-naphthol of the formula (1'),

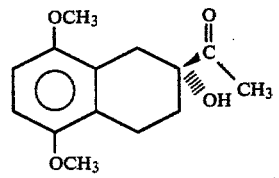

(1')

The compound of the formula (1) or (1') is one which is extraordidnarily useful as a material for the synthesis of the anthracycline type antibiotics adriamycin (2), daunorubicin (3), etc., which are attracting keen interest lately in their prominent carcinostatic activities (F. Arcamone: Lloydia, 40, 45 (1977); T. R. Kelly: "Synthetic Approaches to Anthracycline Antibiotics" in "Annual Reports in Medicinal Chemistry", Am. Chem. Soc., 1979). From the compound of the formula (1'), there can be synthesized adriamycinone (4) and daunomycinone (5) which are the aglycones of (2) and (3), respectively. Also, there has been established a route for the synthesis of (2) and (3) from the aglycones (4) and (5), respectively (C. M. Wong, et al: Can. J. Chem., 49, 2712 (1971); C. M. Wong, et al: Ibid., 51, 466 (1973); T. H. Smith, et al: J. Org. Chem., 42, 3653 (1977)). Further, 4-demethoxy adriamycin (6) and 4-demethoxy daunorubicin (7), which are the non-natural type anthracyclines with few unfavorable side effects such as cardiac trouble, can be synthesized by using the compound (1') as starting material (F. Arcamone, et al: Cancer Treat. Rep., 60, 829 (1976); F. Arcamone, et al: German Offen. No. 2,601,785; F. Arcamone: Lloydia, 40, 45 (1977)).

As stated above, the compound of the formula (1), particularly (1'), is a very important compound as a starting material for the preparation of natural and non-natural type anthracyclines.

As explained above, the reducing agent of this invention can serve as a useful reagent in the first step of a process for producing a compound of the formula (1) or (1') effectively by using the compound of the formula (IV) as a starting material.

A process for obtaining the compound of the formula (1) or (1') from the compound of the formula (V) or (V') is shown below by way of reference.

The double bond between 1-position and 2-position of the compound of the formula (V) or (V') is epoxidized to form 2-(1'-hydroxy)ethyl-5,8-dimethoxy-1,2-epoxy-1,2,3,4-tetrahydronaphthalene or 2(S)-(1'(S)-hydroxy)ethyl-5,8-dimethoxy-1(S), 2(S)-epoxy-1,2,3,4-tetrahydronaphthalene of the formula (VI) or (VI'),

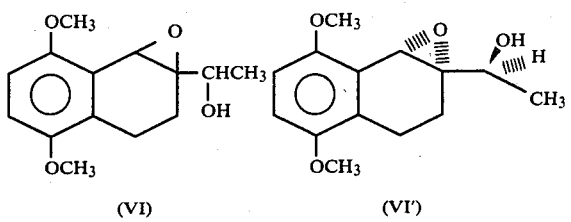

(VI)    (VI')

Then, the 1,2-epoxy portion

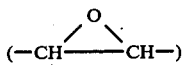

of this compound is reduced to obtain 2-(1'-hydroxy)ethyl-5,8-dimethoxy-1,2,3,4-tetrahydro-2-naphthol or (−)-2(R)-(1'(S)-hydroxy)ethyl-5,8-dimethoxy-1,2,3,4-tetrahydro-3(R)-naphthol of the formula (VII) or (VII'),

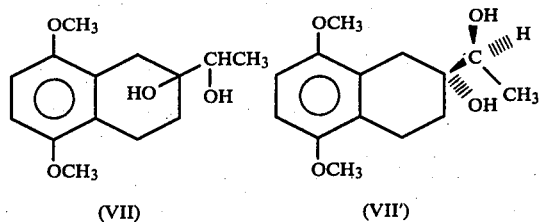

(VII)    (VII')

and then the 1'-hydroxy portion (>CHOH) of this compound is oxidized to obtain the compound of the formula (1) or (1').

The ordinary double bond epoxidation reaction formula

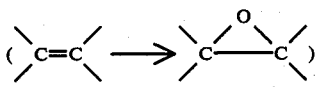

is used for the 1-position and 2-position double bond epoxidation reaction in the first stage of the above-said process. As the oxidizing agent, there may be ordinarily used a reagent prepared from t-butylhydroperoxide, cumenehydroperoxide, etc., in the presence of a catalyst such as molybdenum dioxyacetylacetonate (MoO$_2$(acac)$_2$), vanadium oxyacetylacetonate (VO(acac)$_2$), etc. (K. B. Scharpless et al: J. Am. Chem. Soc., 95, 6136 (1973); H. Yamamoto, et al: Bull. Chem. Soc. Japan, 52, 1701 (1979)) as well as the organic peracids such as perbenzoic acid, m-chloroperbenzoic acid, peracetic acid, etc. Usually, the reaction is carried out in an aromatic hydrocarbon solvent such as benzene, toluene, etc. or a halogenated hydrocarbon solvent such as chloroform, methylene chloride, etc., at a temperature of −20° to +20° C. for a period of 30 minutes to 4 hours.

Since the compound (VI) obtained in this reaction is unstable, it is usually immediately passed on as a crude compound to the ensuing step without refining.

When the compound of the formula (V') having 100% optical purity is oxidized in a solvent such as benzene, etc. by using a reagent prepared from t-butylhydroperoxide in the presence of vanadium oxyacetylacetonate (catalyst), there can be obtained an optically active compound (VI'). Usually, such compound is obtained as a mixture with small quantities of its 1(R)-, 2(R)- isomers (see Referential Example), and since this mixture is an unstable oil, it is immediately subjected to the ensuing step without refining.

The reduction reaction of the 1,2-epoxy portion of the compound (VI) in the second stage can be accomplished by a usual reduction reaction of an epoxy

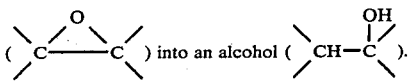

This reaction is performed in an ether type solvent such as tetrahydrofuran, etc. or an aromatic hydrocarbon type solvent such as benzene, toluene, etc., by using usually lithium aluminum hydride, sodium bis(2-methoxyethoxy) aluminum hydride or the like as reducing agent at a temperature of −20° to +25° C. for a period of 1-4 hours.

When the optically active compound (VI') is subjected to this reduction reaction, there is obtained an optically active compound of the formula (VII'). When the above-said reduction reaction is carried out by using the compound (VI') mixed with small quantities of 1(R), 2(R) isomers, there is normally obtained a compound (VII') mixed with a 2(S)-epimer, but this crude product can be refined by means of column chromatography, recrystallization, etc. Said compound, in the form of a mixture with a 2(S)-epimer, may be immediately subjected to the succeeding oxidation reaction.

The oxidation of the 1'-hydroxy portion (>CHOH) of the compound (VII) in the third step is usually accomplished by using the method of oxidizing a secondary alcohol into a corresponding ketone (>CHOH→>C=O). As the oxidizing agent, there is usually used chromic acid-sulfuric acid, pyridinium chlorochromate (E. J. Corey, et al: Tetrahedron Letters, 1975, 2647), dimethylsulfoxide-dicyclohexylcarbodiimide-trifluoroacetic acid-pyridine (K. E. Pfitzner, et al: J. Am. Chem. Soc., 87, 5661, 5670 (1965)), silver carbonate-Celite (Fetizon reagent) (Fetizon, et al: J. Org. Chem., 36, 1339 (1971)), dimethylsulfoxide-sulfur trioxide (SO$_3$) pyridine complex-triethylamine (J. R. Parikh, et al: J. Am. Chem. Soc., 89, 5505 (1967)) or the like, and the reaction is usually accomplished in a solvent such as acetone, dichloromethane, dimethylsulfoxide, benzene, etc., at a temperature of 0°–80° C. for a period of 1–24 hours.

Oxidation of the optically active compound (VII') by use of the Fetizon reagent provides the optically active compound (1') of this invention. When the compound (VII') mixed with 2(S)-epimer as said above is used, there is obtained the compound (1') mixed with 2(S)-epimer.

As described above, after reducing 2-acetyl-5,8-dimethoxy-3,4-dihydronaphthalene (IV) by using the reducing agent of this invention to obtain the compound (V) or (V') and subjecting this reduced compound to a simple reaction operation which can be practiced industrially, there can be obtained 2-acetyl-5,8-dimethoxy-1,2,3,4-tetrahydro-2-naphthol (1) which can serve as a very useful starting material for the synthesis of the anthracycline antibiotics. It is particularly noteworthy that the optically active body (1') of the compound (1) can be obtained in 100% optical purity. The compound of the formula (IV) can be readily prepared from 5,8- dimethoxy-3,4-dihydro-2-naphthoic acid (S. Terashima, et al: Chem. Pharm. Bull., (Tokyo), 27, 2351 (1979)).

It is to be noted here that the compound (1) includes 2(R)-body, 2(S)-body or mixtures thereof, compound (V) includes 1′(S)-body, 1′(R)-body or mixtures thereof, compound (VI) includes 1′(S),1(S),2(S)-body, 1′(S),1(R),2(R)-body, 1′(R),1(R),2(R)-body, 1′(R),1(S),2(S)-body or mixtures of optional combinations of theses four types of isomers, and compound (VII) includes 1′(S),2(R)-body, 1′(S),2(S)-body, 1′(R),2(S)-body, 1′(R),2(R)-body and mixtures of optional combinations of these four types of isomers. Concerning the process of (IV→V→VI→VII→1), there exist the following relations:

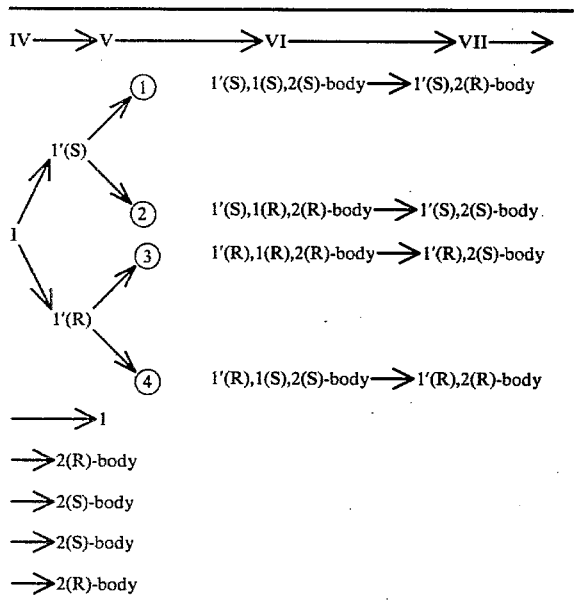

The present invention is described in further detail hereinbelow with reference to the examples, but the present invention is not limited to these examples.

EXAMPLE 1

Synthesis of (−)-N-methylephedrine

Ephedrine hydrochloride (30.3 g, 0.15 mol) was dissolved in warm water (60 ml) there was, then added thereto a 40% sodium hydroxide aqueous solution (15 ml, 0.15 mol) and 85% formic acid (21.7 g, 0.4 mol) and the mixture refluxed under heating, and to this solution was added dropwise at 35% formalin solution (15 g, 0.18 mol) over 20 minutes. Thereafter, refluxing under heating was continued for 3 hours and the reaction solution was concentrated to ½ of its original volume and then added thereto was a 40% sodium hydroxide aqueous solution to adjust the pH to about 11. The resultant precipitated crystals were filtered out and recrystallized from methanol. Yield: 23 g (84%); m.p.: 86.5°–87.5° C. $[\alpha]_D^{20} = -29.5°$ (C=4.54, MeOH).

EXAMPLE 2

Preparation of modified lithium aluminum hydride type reducing agent

Dry ether (10 ml) was added into lithium aluminum hydride (206 mg, 5.4 mmol) in an argon atmosphere and the mixture was refluxed under heating, mixed with a dry ether (10 ml) solution of (−)-N-methylephedrine (1 g, 5.56 mmol) and reacted under stirring at the same temperature for one hour. To this reaction solution was further added a dry ether (10 ml) solution of N-ethylaniline (1.35 g, 11.12 mmol) to perform reaction under stirring at the same temperature for one hour, whereupon a total of 363 ml of hydrogen gas was generated and an ether solution of a modified lithium aluminum hydride type reducing agent having the following physical properties was obtained.

IR absorption spectrum (neat): $v$; 3420, 2960, 1780, 1600, 1500, 1450, 1380 cm$^{-1}$

EXAMPLE 3

Reduction of acetophenone

The reaction solution of Example 2 was cooled to −78° C., added thereto was a dry ether (10 ml) solution of acetophenone (360 mg, 3 mmol) and the mixture reacted under stirring at the same temperature for 3 hours.

After the reaction was over, 1 N hydrochloric acid (24 ml) was added to separate the ether layer and this ether layer was washed with 10% hydrochloric acid (20 ml) and a saturated saline solution (20 ml × 3), then dried with anhydrous magnesium sulfate and filtered, and the filtrate was concentrated under reduced pressure to obtain (S)(−)-1-phenylethanol. Yield: 330 mg (90%), $[\alpha]_D^{20} = -36.4°$ (C=7.45, cyclopentane), optical purity: 84%.

The aqueous layer and the 10% hydrochloric acid washings were joined and the joined solution was mixed with a 10% sodium hydroxide solution (30 ml) to adjust the pH to about 11 and extracted with ethyl acetate (50 ml × 3). The extract was washed with a saturated saline solution (50 ml × 3), dried and then ethyl acetate was distilled off to obtain a mixture of N-methylephedrine or N-ethylaniline. Yield: 2.4 g (100%). Said two substances can be recovered separately by distilling the mixture under reduced pressure.

N-methylephedrine: b.p.: 120° C./0.01 mmHg; yield: 850 mg, $[\alpha]_D^{20} = -29.0°$ (C=6.50, MeOH). N-ethylaniline: b.p.: 87°–90° C./15 mmHg, yield: 1.3 g.

REFERENTIAL EXAMPLE 4

Various ketone compounds were reduced in the same way as in Referential Example 3 to obtain the results as shown in Table 1.

TABLE 1

| Run | Substrate | Yield (%) | Optical purity (%) (R, S) |
|---|---|---|---|
| 1 | | 96 | 90(S) |
| 2 | | 95 | 78(S) |
| 3 | | 100 | 80(S) |
| 4 | | 88 | 71(S) |
| 5 | | 96 | 51(S) |

TABLE 1-continued

| Run | Substrate | Yield (%) | Optical purity (%) (R, S) |
|---|---|---|---|
| 6 | (tetralone) | 98 | 67(R) |
| 7 | (phenylacetone) | 90 | 41(S) |
| 8 | (cyclohexyl methyl ketone) | 90 | 35(S) |

EXAMPLE 5

Reduction of benzylideneacetone

Dry ether (10 ml) was added to lithium aluminum hydride (376 g, 9.9 mmol) in an argon atmosphere, and the mixture was refluxed under heating, mixed with a dry ether (20 ml) solution of (−)-N-methylephedrine (1.83 g, 10.2 mol) and reacted under stirring at the same temperature for one hour. To this reaction solution was added a dry ether (10 ml) solution of N-ethylaniline (2.47 g, 20.4 mmol) and it was further reacted under stirring at the same temperature for one hour.

The reaction solution was cooled to −78° C., added with a dry ether (5 ml) solution of benzylideneacetone (439 mg, 3 mmol) and reacted under stirring at the same temperature for 3 hours. After completion of the reaction, 1 N hydrochloric acid (42 ml) was added to separate the ether layer and the ether layer was washed with 1% hydrochloric acid (20 ml×2) and a saturated saline solution (20 ml×3), dried with anydrous magnesium sulfate and filtered, and the filtrate was concentrated under reduced pressure to obtain (S)(−)-benzylideneisopropanol. Yield: 435 mg (98%), $[\alpha]_D^{20}=24.2°$ (C=5.16, CHCl$_3$), optical purity: 98%.

REFERENTIAL EXAMPLE 6

Various ketone compounds were reduced in the same way as in Example 5. The results are shown in Table 2.

TABLE 2

| Run | Substrate | Yield (%) | Optical purity (%) (R.S.) |
|---|---|---|---|
| 1 | (benzylideneacetone) | 100 | >90* |
| 2 | (2-acetylnaphthalene) | 100 | >90* |
| 3 | (5,8-dimethoxy-3,4-dihydronaphthalenyl methyl ketone, OCH$_3$/OCH$_3$) | 100 | 92(S) |
| 4 | (cyclohexenyl methyl ketone) | 92 | 78(S) |
| 5 | (cyclohexenone) | 58 | 32(S) |
| 6 | (methylcyclohexenone) | 73 | 58* |
| 7 | (methylcyclohexenone) | 88 | 24* |
| 8 | n-C$_4$H$_9$—C(=O)—C≡CH | 88 | 76(S) |

*Optical purity was measured by using an NMR shift reagent (Eu(hfc)$_3$).

EXAMPLE 7

Lithium aluminum hydride (1.44 g, 38 mmol) was suspended in ether (70 ml) under an argon stream, and to this suspension was added an ether solution (100 ml) of (-)-N-methylephedrine (6.81 g, 38 mmol), followed by refluxing under heating and stirring for one hour, further addition of an ether solution (60 ml) of N-ethylaniline (9.21 g, 76 mmol) and refluxing under heating and stirring for an additional one hour to thereby prepare a reducing reagent was conducted.

EXAMPLE 8

Preparation of (−)-2-(1'(S)-hydroxy)ethyl-5,8-dimethoxy-3,4-dihydronaphthalene (V')

An ether solution of the reducing reagent of Example 7 was cooled to −78° C., added thereto slowly was an ether solution (200 ml) of the compound (IV') (2.20 g, 9.47 mmol) and the product was reacted under stirring at the same temperature for 3 hours. Upon completion of the reaction, the reaction mixture was mixed with 1 N hydrochloric acid (152 ml, 152 mmol) and extracted with ethyl acetate (150 ml×2). The obtained extracts were joined, washed with a 1% hydrochloric acid aqueous solution (150 ml×2), a 5% sodium bicarbonate solution (150 ml), water (150 ml×2) and a saturated saline solution (150 ml) in that order and then dried with anhydrous magnesium sulfate. The resulting product was filtered and distilled to obtain the crude compound (V') in the form of light yellow crystals (2.58 g, quantitative yield), $[\alpha]_D^{20}=-17.8°$ (C=1.83, ethanol).

Supposing that the optical purity of the compound (V') with $[\alpha]_D^{20}=-20.5°$ (C=1.07, ethanol) obtained by subjecting the above-said sample to the following operation is 100%, the optical purity of said sample is 87%. Recrystallization of the obtained crystals from hexane (130 ml) gave the colorless needlelike crystals of the pure compound (V') with 100% optical purity (yield: 1.8 g, 81%; m.p.: 88°–89° C.; $[\alpha]_D^{20}=-20.5°$ (C=1.07, ethanol)). IR: $\nu_{max}^{CHCl_3}$ cm$^{-1}$: 3600, 1260, 1100 (alcohol). NMR (in CDCl$_3$)δ: 1.32 (3H, d, J=6 Hz, CH(OH)CH$_3$), 2.00–2.36 (2H, m, CH$_2$C=), 2.12 (1H, s, OH), 2.64–2.88 (2H, m, CH$_2$CH$_2$C=), 3.74 (6H, s, two OCH$_3$), 4.40 (1H, q, J=6 Hz, CH(OH)), 6.60 (2H, s, aromatic protons), 6.72 (1H, brs, =CH). Anal.: Calcd. for C$_{14}$H$_{18}$O$_3$: C, 71.77, H, 7.74, Found: C, 71.57, H, 7.76.

The 1 N hydrochloric acid layer remaining after extraction with ethyl acetate was made alkaline (pH>12) with a 10% sodium hydroxide aqueous solution and extracted with ethyl acetate (150 ml×2). The ethyl acetate extracts were joined, washed with a saturated saline solution (150 ml) and dried with anhydrous potassium carbonate, followed by filtration and distillation to obtain a 1:2 mixture of (−)-N-methylephedrine and N-ethylaniline as a light yellow oily product (16.3 g, quantitative recovery).

EXAMPLE 9

Preparation of the compound (1′) by using the compound (V′) as a starting material (1) (−)-2(R)-(1′(S)-hydroxy)ethyl-5,8-dimethoxy-1,2,3,4-tetrahydro-2(R)-naphthol (VII′):

The compound of the formula (V′) (m.p.: 88°–89° C., $[\alpha]_D^{20} = -20.5°$ (C=1.07, ethanol)) (703 mg, 3.00 mmol) and vanadium oxyacetylacetonate (11 mg, 0.042 mmol) were dissolved in benzene (55 ml) under an argon stream, and the mixed solution was mixed with a benzene solution of t-butylhydroperoxide (22 mg/ml, 13.5 ml, 3.3 mmol) at room temperature under stirring and reacted at the same temperature for 1.5 hours. Upon completion of the reaction, benzene was distilled off to obtain a mixture of crude compound (VI′) and 1(R),2(R) isomer thereof as an unstable oily product. This product was dissolved in tetrahydrofuran (40 ml) and this tetrahydrofuran solution was added to a suspension of lithium aluminum hydride (456 mg, 12 mmol) in tetrahydrofuran (40 ml), and the suspension was stirred at room temperature for 2 hours. Upon completion of the reaction, the reaction mixture was mixed with a 10% sodium hydroxide aqueous solution (65 ml) and the water layer was extracted with ethyl acetate (50 ml×3). The extracts were joined, washed with water (50 ml×3) and a saturated saline solution (100 ml) and dried with anhydrous magnesium sulfate. The resulting product was filtered and distilled to obtain a mixture of crude compound (VII′) and 2(S)-epimer thereof in the form of colorless crystals (730 mg, 97% from (V′)).

A part (380 mg) of the colorless crystals (730 mg) was separated and refined by column chromatography (silica gel, solvent; benzene-ethyl acetate (1:1)) to obtain a mixture of the compound (VII′) and its 2(S)-epimer as colorless needle-like crystals (325 mg, 82% from (V′)), m.p.: 140°–150° C., $[\alpha]_D^{20} = -39.3°$ (C=1.04, ethanol). Both IR and NMR spectra of this product agreed with those of the pure compound (VII′) shown below. Since the compound (1′) with 90% optical purity could be obtained from said product, the ratio of the compound (VII′) to its 2(S)-epimer, that is, the ratio of the compound (VI′) to its 1(R),2(R)-epimer was calculated to be 95:5.

The remainder (350 mg) of said colorless crystals (730 mg) was crystallized from ether (35 ml) to obtain the pure compound (VII′) in the form of colorless needle-like crystals (252 mg, 70%), m.p.: 154°–155° C., $[\alpha]_D^{20} = -49.7°$ (C=0.50, ethanol). IR $\nu_{max}^{CHCl_3}$ cm$^{-1}$: 3580, 1260, 1105, 1090 (alcohol). IR $\nu_{max}^{KBr}$ cm$^{-1}$: 3360, 1260, 1085 (alcohol). NMR (in CDCl$_3$—CD$_3$OD)δ: 1.23 (3H, d, J=6 Hz, CH(OH)C$\underline{H}_3$), 1.40–2.05 (2H, m, C$\underline{H}_2$C(OH)), 2.50–2.88 (4H, m, C$\underline{H}_2$C(OH)CH$_2$C$\underline{H}_2$), 3.20 (2H, s, O$\underline{H}$X2), 3.62 (1H, q, J=6 Hz, C$\underline{H}$(OH)CH$_3$), 3.72(3H, s, OC$\underline{H}_3$), 3.74 (3H, s, OCH$_3$), 6.60 (2H, s, aromatic protons). Anal.: Calcd. for C$_{14}$H$_{20}$O$_4$: C, 66.64, H, 7.99, Found: C, 66.48, H, 8.06.

(2) (−)-2(R)-acetyl-5,8-dimethoxy-1,2,3,4-tetrahydro-2(R)-naphthol (1′):

A mixture of the compound (VII′) and its 2(S)-epimer showing (m.p.: 140°–150° C., $[\alpha]_D^{20} = -39.3°$ (C=1.04, ethanol)) (135 mg, 0.54 mmol) was dissolved in benzene (13 ml), then mixed with Fetizon reagent (1 mmol/g, 2.7 g, 2.7 mmol) and refluxed under heating for 30 minutes. After the completion of the reaction, silver-Celite was filtered out and washed with benzene (40 ml). The washed solutions were joined and the filtrate was concentrated under reduced pressure to obtain a reddish brown oily product (140 mg). This product was separated and refined by thin-layer chromatography (silica gel, solvent: benzene-ethyl acetate (5:1)) to obtain the compound (1′) as colorless crystals (105 mg, 84%), m.p.: 123°–127° C., $[\alpha]_D^{20} = -42.5°$ (C=0.89, chloroform). The IR and NMR spectra of this product agreed with those of the pure preparation shown below. Supposing that the optical purity of the compound (1′) with $[\alpha]_D^{20}$ of −47.1° (C=1.11, chloroform) is 100%, then the optical purity of this product is 90%.

A similar treatment was performed on the pure compound (VII′) (m.p.: 154°–155° C., $[\alpha]_D^{20} = -49.6°$ (C=1.08, ethanol)) (134 mg, 0.53 mmol) and the benzene filtrate was concentrated under reduced pressure to obtain a reddish brown oily product (130 mg). This product was separated and refined by thin-layer chromatography in the same way as in the above to obtain the pure compound (1′) as colorless crystals (91 mg, 69%), m.p.: 127°–128.5° C., $[\alpha]_D^{20} = -44.0°$ (C=1.92, chloroform). Two times of recrystallizations of this product from chloroform-ether gave an elemental analysis sample of the compound (1′) in the form of colorless needle-like crystals with m.p.: 128°–129° C., $[\alpha]_D^{20} = -47.1°$ (C=1.11, chloroform) (S. Terashima, et al: Chem. Pharm. Bull. (Tokyo), 27 2351 (1979)), m.p.: 128°–129° C., $[\alpha]_D^{20} = -48.2°$ (C=0.982, chloroform)). IR $\nu_{max}^{CHCl_3}$ cm$^{-1}$: 1710 (ketone). NMR (in CDCl$_3$)δ: 1.86–2.10 (2H, m, C$\underline{H}_2$C(OH)), 2.29 (3H, s, COC$\underline{H}_3$), 2.70–3.10 (4H, m, C$\underline{H}_2$CH$_2$C(OH)C$\underline{H}_2$), 3.58 (1H, s, O$\underline{H}$), 3.72 (3H, s, OC$\underline{H}_3$), 3.76 (3H, s, OC$\underline{H}_3$), 6.62 (2H, s, aromatic protons). The spectra of these products agreed with those of the literature (S. Terashima, et al: Chem. Pharm. Bull (Tokyo), 27, 2351 (1979)).

What is claimed is:

1. A novel modified lithium aluminum hydride type reducing agent obtained by reacting one equivalent of lithium aluminum hydride with one equivalent of an optically active N-substituted ephedrine of the formula,

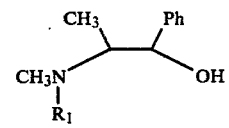

(wherein R$_1$ is a C$_1$-C$_4$ alkyl or benzyl group and Ph is phenyl group) and two equivalents of an N-substituted aniline of the formula,

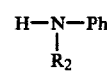

(wherein R$_2$ is a C$_1$-C$_4$ straight-chain alkyl or phenyl group and Ph is phenyl group).

2. The reducing agent according to claim 1, wherein N-substituted ephedrine is optically active N-(C$_1$-C$_4$)alkylephedrine.

3. The reducing agent according to claim 1, wherein the N-substituted ephedrine is optically active N-methylephedrine.

4. The reducing agent according to claim 1, wherein optically active N-substituted ephedrine is a (−)-isomer.

5. The reducing agent according to claim 1, wherein optically active N-substituted ephedrine is a (−)-N-($C_1$–$C_4$)alkylephedrine.

6. The reducing agent according to claim 1, wherein optically active N-substituted ephedrine is a (−)-N-methylephedrine.

7. The reducing agent according to claim 1, wherein N-substituted aniline is N-($C_1$–$C_4$)alkylaniline.

8. The reducing agent according to claim 1, wherein the N-substituted aniline is N-ethylaniline.

9. A reducing agent according to claim 1 wherein the N-substituted ephedrine is optically active N-methylephedrine and wherein the N-substituted aniline is N-ethylaniline.

* * * * *